United States Patent [19]

Hammen

[11] 4,062,844

[45] Dec. 13, 1977

[54] PROCESS FOR PREPARING HYPOTENSIVE 2-(4-AROYLPIPERAZIN-1-YL)-AMINO-6,7-DIMETHOXYQUINAZOLINES

[75] Inventor: Philip D. Hammen, East Lyme, Conn.

[73] Assignee: Pfizer Inc., New York, N.Y.

[21] Appl. No.: 724,707

[22] Filed: Sept. 20, 1976

[51] Int. Cl.$^2$ ............................................. C07D 239/95
[52] U.S. Cl. ............................................. 260/256.4 Q
[58] Field of Search ................................. 260/256.4 Q

[56] References Cited

U.S. PATENT DOCUMENTS 3,511,836  5/1970  Hess ................................. 260/256.4 Q Primary Examiner—Paul M. Coughlan, Jr.
Attorney, Agent, or Firm—Connolly and Hutz

[57] ABSTRACT

Certain 2-(4-aroylpiperazin-1-yl)-4-amino-6,7-dimethoxyquinazolines are prepared by a novel process wherein certain 2-(4-substituted-piperazin-1-yl)-4-amino-6,7-dimethoxyquinazoline intermediates wherein said substituent is cyano, certain carbon-oxygen double bond containing groups or certain carbon-nitrogen double bond containing groups, are reacted with certain metalloaryl compounds followed by hydrolysis. The products are known hypotensive agents. Certain of the process intermediates are novel compounds.

7 Claims, No Drawings

PROCESS FOR PREPARING HYPOTENSIVE 2-(4-AROYLPIPERAZIN-1-YL)-AMINO-6,7-DIMETHOXYQUINAZOLINES

BACKGROUND OF THE INVENTION

1. Field of the Invention

The invention relates to a new chemical process for preparing certain known chemical compounds, valuable in the art by virtue of their ability to lower blood pressure in hypertensive mammals. More specifically, these hypotensive agents are certain 2-(4-aroylpiperazin-1-yl)-4-amino-6,7-dimethoxyquinazolines, use of which is taught in U.S. Pat. No. 3,511,836. The invention also relates to certain novel 2-(4-substituted-piperazin-1-yl)-4-amino-6,7-dimethoxyquinazolines wherein said substituent is cyano, or one of certain N,N-disubstituted carbamyl, imido ester, imido thiolester or amidino groups, which are useful as intermediates in the process of the invention.

2. Description of the Prior Art

U.S. Pat. No. 3,511,836 discloses several processes for the preparation of 2-(4-substituted piperazin-1-yl)-4-amino-6,7-dimethoxyquinazolines. For example, by the reaction of 2-chloro-4-amino-6,7-dimethoxyquinazoline with the appropriate 1-substituted piperazine, by reaction of a 2-(4-substituted piperazin-1-yl)-4-chloro-6,7-dimethoxyquinazoline with ammonia or by alkylation, alkanoylation, aroylation or alkoxylation of 2-(2-piperazinyl)-4-amino-6,7-dimethoxyquinazoline. U.S. Pat. No. 3,669,968 teaches the preparation of 2-(4-substituted piperazin-1-yl)-4-amino-6,7,8-trimethoxyquinazolines via reaction of 2-chloro-4-amino-6,7,8-trimethoxyquinazoline with the appropriate 1-substituted piperazine.

In U.S. Pat. No. 3,935,213 processes are disclosed whereby 2-(4-substituted-piperazin-1-yl)-4-amino-6,7-dimethoxyquinazolines and the corresponding 6,7,8-trimethoxyquinazolines are produced by either: (1) reaction of the appropriate 4,5-dimethoxy-substituted or 3,4,5-trimethoxy-substituted 2-aminobenzonitrile with certain 1,4-disubstituted piperazines; or (2) reaction of the appropriate 4,5-dimethoxy- or 3,4,5-trimethoxy-substituted 2-aminobenzamidine with the same 1,4-disubstituted piperazines.

2-(4-Alkoxycarbonylpiperazin-1-yl)-4-amino-6,7-dimethoxyquinazolines which are useful intermediates in the process of the invention are disclosed and claimed in U.S. Pat. No. 3,511,836. However, other intermediates which are useful in the instant process are novel compounds.

SUMMARY OF THE INVENTION

The invention relates to a novel process for preparing compounds of formula (I)

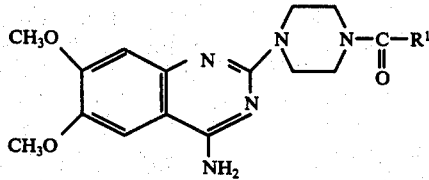

which comprises the steps of a. contacting one mole of a first reactant of formula (II)

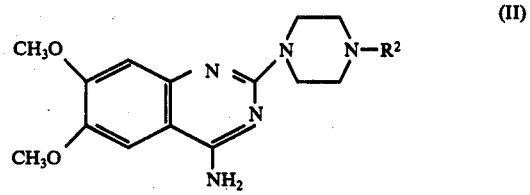

wherein $R^2$ is a member selected from the group consisting of —CN,

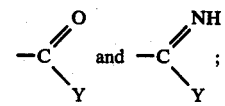

Y is a member selected from the group consisting of —OR$^3$, —SR$^3$ and —NR$^4$R$^5$; R$^3$ is a member selected from the group consisting of alkyl having from one to four carbon atoms and phenyl; and R$^4$ and R$^5$ are the same or different and are each selected from the group consisting of alkyl having from one to four carbon atoms and phenyl; with from about one to three moles of a second reactant of the formula R$^1$M wherein R$^1$ is a member selected from the group consisting of furyl, phenyl and thienyl; and M is a member selected from the group consisting of Li, Na and MgX where X is Cl, Br, or I; under substantially anhydrous conditions in the presence of a reaction inert organic solvent at a temperature from about −80° to 65° C.; and b. hydrolyzing the reaction mixture obtained in step a.

An especially preferred process is that wherein R$^2$ is —CN or —CONR$^4$R$^5$ and M is Li when carried out at a temperature from about −60° to −20° C. and equimolar amounts of said reactants are contacted. Especially preferred as CONR$^4$R$^5$ is that wherein R$^4$ and R$^5$ are each methyl and that wherein R$^4$ and R$^5$ are each phenyl.

Whereas the instant process is useful for the preparation of said known hypotensive agents of formula (I), it is especially useful in the preparation of the particularly valuable congener wherein R$^1$ is 2-furyl; namely, 2-[4-(2-furoyl)piperazin-1-yl]-4-amino-6,7-dimethoxyquinazoline, known in the art as prazosin. Prazosin has been shown to have therapeutic utility in man; see Cohen, *Journal of Clinical Pharmacology*, 10, 408 (1970).

The invention also pertains to the novel and useful intermediates of formula (III)

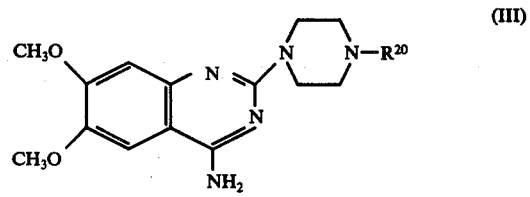

wherein R$^{20}$ is a member selected from the group consisting of —CN, —CONR$^4$R$^5$ and

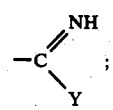

and Y is a member selected from the group consisting of —OR$^3$, —SR$^3$ and —NR$^4$R$^5$; R$^3$, R$^4$ and R$^5$ are as previously defined. Especially valuable intermediates of formula (III) are those wherein R$^{20}$ is —CN, —CON(CH$_3$)$_2$ and —CON(C$_6$H$_5$)$_2$.

DETAILED DESCRIPTION OF THE INVENTION

It is an object of the invention to provide a process for the preparation of the valuable hypotensive agents of formula (I) by contacting a compound of formula (II) with a compound of formula R$^1$M followed by hydrolyzing the reaction mixture thus obtained. The reaction between compounds of formulae (II) and R$^1$M is carried out in the presence of a reaction inert organic solvent. An appropriate solvent is one which will serve to substantially dissolve or disperse the reactants and will not adversely interact with reactants or products of the reaction. Examples of such solvents are ethers such as diethyl ether, diisopropyl ether, di-n-butyl ether, methyl isobutyl ether, tetrahydrofuran, tetrahydropyran, dioxane, ethyleneglycol dimethyl ether, diethyleneglycol dimethyl ether and anisole; hydrocarbons such as hexane, heptane, cyclohexane, 1-decene, benzene and xylene and tertiary amines such as triethylamine as well as mixtures thereof.

While the reaction can be carried out over a wide range of temperature, it is preferred to employ temperatures in the range of about −80° to 65° C. When aryllithium compounds of formula R$^1$Li are employed an especially preferred temperature is in the range of about −60° to −20° C. When Grignard reagents of the formula R$^1$MgX are employed temperatures of about 0° to 65° C. are especially preferred.

The time required for the reaction to reach substantial completion varies according to factors such as the temperature and the precise nature of the reactants of formulae (II) and R$^1$M. However, the reaction is ordinarily substantially complete in a matter of a few minutes to several hours. As will be appreciated by one skilled in the art, at lower temperatures longer reaction times are required, while at higher temperatures the reaction is completed in a shorter time.

As will be recognized by one skilled in the art, this step of the process of the invention is carried out under substantially anhydrous conditions.

The reaction between the reactants of formulae (II) and R$^1$M forms an intermediate which is readily hydrolyzed to provide the desired product of formula (I). The overall reaction is exemplified below for the case wherein R$^2$ is —CN.

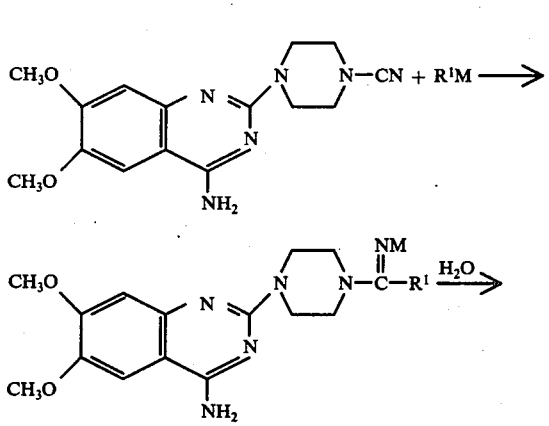

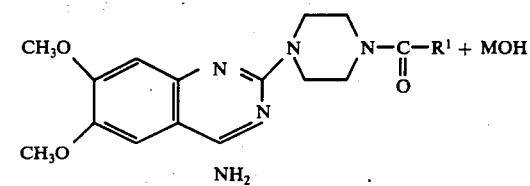

The hydrolysis also serves to decompose any remaining reactant of formula R$^1$M.

The hydrolysis may be carried out with water alone to provide an alkaline mixture or the hydrolysis can be effected by addition of dilute aqueous acids such as hydrochloric, sulfuric, phosphoric and acetic acids or aqueous solutions of acidic salts such as ammonium chloride, ammonium bromide, ammonium dihydrogen phosphate, diammonium hydrogen phosphate, sodium dihydrogen phosphate and triethylamine hydrochloride. The hydrolysis may be carried out over a wide range of temperatures; for example, temperatures in the range of about −20° to 100° C. may be employed. However, for reasons of convenience the hydrolysis is preferably carried out at a temperature at or about room temperature. When room temperature hydrolysis is carried out it is often desirable to cool the reaction mixture during the addition of the water, aqueous acid or aqueous salt solution, as the hydrolysis is exothermic in some cases.

The time required for hydrolyzing the reaction mixture will, of course, vary inversely with the temperature; however, at or about room temperature, hydrolysis is usually complete in from a few minutes to about 2 hours.

After the hydrolysis is substantially complete, the reaction mixture is worked up by standard methods which will be apparent to one skilled in the art. For example, when acid hydrolysis is employed, the aqueous layer is extracted with a water immiscible solvent which can be that employed for the reaction or another solvent such as chloroform, methylene chloride, ethyl acetate, methyl isobutyl ketone and the like. Such extraction removes neutral material as the desired product is soluble in dilute aqueous acids. The aqueous phase is then made alkaline by addition of e.g., sodium hydroxide, potassium hydroxide or sodium carbonate, and again extracted, the extracts evaporated to a small volume and precipitated by addition of an insolubilizing solvent such as hexane, heptane or petroleum ether. The precipitated product is then collected by filtration and may be further purified by standard methods such as recrystallization or by silica gel column chromatography. When the hydrolysis step is carried out with water alone, the resulting mixture is alkaline and the aqueous layer may be extracted with one of the above mentioned solvents and the product-containing extracts worked up as described for the acid hydrolysis.

When the process of the invention is carried out with compounds of the formula R$^1$M wherein R$^1$ is furyl, phenyl or thienyl and M is lithium or sodium, it is preferred to employ the reactants of formulae (II) and R$^1$M in approximately equimolar amounts for reasons of economy. However, when the compounds R$^1$M are the well-known Grignard reagents wherein M is MgX (X is chloro, bromo or iodo) are employed, up to three moles of the Grignard reagent, R$^1$MgX, may be required due to the interaction of the reagent with the quinazoline-4-amino group in the compound of formula (II) or its tautomers such as the structure (IIa)

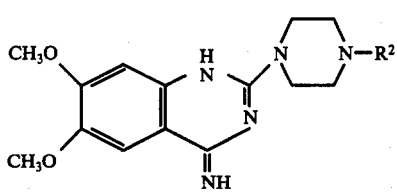

(IIa)

to form II.(MgX)$_n$ or IIa.(MgX)$_n$ and $n$ moles of R$^1$H wherein $n$ is 1 or 2.

Especially preferred is the process of the invention when carried out with compounds of formula (II) wherein R$^2$ is —CN or —CONR$^4$R$^5$ and employing an equimolar amount of an aryllithium reagent of formula R$^1$Li. Especially preferred as —CONR$^4$R$^5$ are —CON(CH$_3$)$_2$ and —CON(C$_6$H$_5$)$_2$.

The reactants of formula R$^1$M employed in the process of the reaction are generally prepared from the halogen compounds R$^1$X where X is chloro, bromo or iodo. Phenyllithium and phenylmagnesium bromide are commercially available. Phenylsodium is prepared from chlorobenzene and metallic sodium by the method described in Fieser, "Reagents for Organic Synthesis", John Wiley and Sons, Inc., 1967, page 848. Phenylmagnesium chloride and phenylmagnesium iodide are prepared by well-known methods; see, for example, the discussion of Grignard reagents in Fieser, loc. cit., page 415 ff. and references given therein. The preparation of the 2-thienylmagnesium halides, 3-thienylmagnesium halides, 2-furylmagnesium halides and 3-furylmagnesium halides are similarly accomplished. The 2-halothiophenes are commercially available as are 3-bromothiophene and 3-bromofuran. 2-Chlorofuran and 2-bromofuran may be obtained from the corresponding 5-halofuran-2-carboxylic acids by the method of Shepard et al., *Jour. Am. Chem. Soc.*, 52, 2083 (1930). 2-Iodofuran is provided by the procedure of Gilman et al., *Jour. Am. Chem. Soc.*, 54, 733 (1932). 2-Thienyllithium and 3-thienyllithium are obtained from the corresponding halothiophenes, preferably the bromothiophenes, by reacting them with n-butyllithium in one of the above mentioned reaction inert solvents employed in the process of the reaction, e.g., ethyl ether, hexane or tetrahydrofuran. The thienylsodium compounds are prepared from the corresponding halothiophenes and finely divided sodium in one of the above reaction inert organic solvents.

The 2-furylsodium reagent can be prepared from furan and benzylsodium by the method described by Morton et al., *Jour. Am. Chem. Soc.*, 68, 93 (1946); 3-furylsodium and 2-furylsodium can be generated by reacting the appropriate halofuran, e.g. 3-bromofuran with sodium metal in an inert solvent. The corresponding furyllithium reagents can also be prepared from the halofurans such as 3-bromofuran or 2-bromofuran and n-butyllithium. However, the preferred 2-furyllithium reagent is most readily obtained from furan and n-butyllithium.

While the reactants of formula (II) wherein R$^2$ is —COOR$^3$ are disclosed and claimed in U.S. Pat. No. 3,511,836, certain of the remaining compounds of formula (II) are novel and useful intermediates. Said novel intermediates are encompassed in the structure (III)

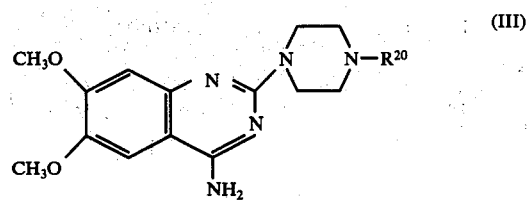

(III)

wherein R$^{20}$ is a member selected from the group consisting of —CN, —CONR$^4$R$^5$ and

wherein Y is a member selected from the group consisting of —OR$^3$, —SR$^3$ and —NR$^4$R$^5$; R$^3$ is selected from the group consisting of alkyl having from one to four carbon atoms and phenyl; R$^4$ and R$^5$ are the same or different and are each selected from the group consisting of alkyl having from one to four carbon atoms and phenyl.

The compounds of formula (II) wherein R$^2$ is —CN, —COOR$^3$, —COSR$^3$ and —CONR$^4$R$^5$ can be prepared by Method A by the reaction of the appropriate 1-substituted-piperazine and 2-chloro(or 2-bromo)-4-amino-6,7-dimethoxyquinazoline (IV). Preparation of the latter starting materials is set forth in U.S. Pat. No. 3,511,836.

Method A:

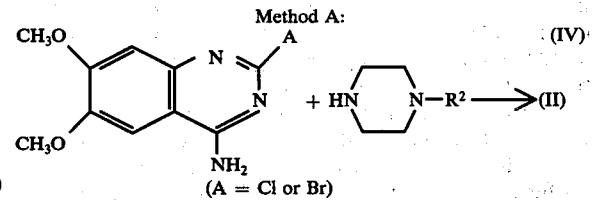

An alternate method, Method B, may be employed for those compounds of formula (II) wherein R$^2$ is —CN, —CONR$^4$R$^5$, —COOR$^3$ and —COSR$^3$.

Method B:

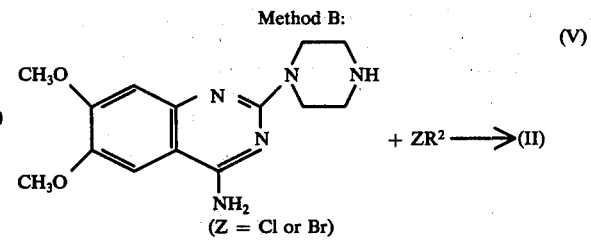

The cyanogen halides are well known compounds and the preferred cyanogen bromide is commercially available. The compounds of formula R$^4$R$^5$NCOCl are commercially available or can be prepared from the appropriate secondary amine of formula R$^4$R$^5$NH and phosgene by the method of Boon, *Jour. Chem. Soc.*, 313 (1947). Likewise, several of the chloroformates, ClCOOR$^3$, are available from commercial sources; those that are not can be prepared by the method of Bergmann et al., *Chem. Ber.*, 65, 1192 (1932). Ethyl chlorothiolformate is an item of commerce; the remaining chlorothiolformates are prepared by the method of Jensen, *Jour. Prakt. Chem.*, 148, 105 (1937). 2-(1-

Piperazinyl)-4-amino-6,7-dimethoxyquinazoline (V) is prepared by the method of U.S. Pat. No. 3,511,836.

When Method A is employed, the 1-substituted piperazine, which can be obtained either from commercial sources or prepared from the above mentioned compounds of formula

where Y is —OR³, —SR³ or —NR⁴R⁵ and an equimolar amount of piperazine, and compound (IV) are combined in equimolar amounts in the presence of a reaction inert organic solvent. The reaction can be carried out over a wide range of temperatures. However, temperatures from about 50° to 150° C. are preferred. Within this preferred temperature range the reaction is ordinarily complete in from 1 to 24 hours. The product may be isolated in the form of the hydrochloride or hydrobromide salt and subsequently converted to free base by standard methods. Alternatively, the reaction mixture can be made alkaline; for example, with sodium hydroxide or potassium hydroxide and the free base isolated by extraction and evaporation of solvent. Examples of suitable reaction inert solvents for this method are the alkanols such as ethanol, butanol, isoamyl alcohol, hexanol and cyclohexanol; N,N-dimethylformamide, N,N-dimethylacetamide, dimethylsulfoxide, diethyleneglycol diethylether, ethyleneglycol n-butyl-ether, and chloroform.

When Method B is employed the compound of formula (V) and an equimolar amount of the appropriate compound of formula ZR² are reacted in the presence of a suitable reaction inert organic solvent. The reaction is preferably carried out at temperatures of from about —20° to 50° C. Examples of suitable solvents for use in Method B are ethyl ether, isopropyl ether, 1,2-dimethoxyethane, diethyleneglycol dimethyl ether, tetrahydrofuran, tetrahydropyran, N,N-dimethylformamide, dimethyl sulfoxide, methylene chloride, chloroform and benzene. The reaction is ordinarily complete in from about 1 to 10 hours. The desired product is isolated by standard methods, such as, for example, pouring the reaction mixture into water, adjusting to an alkaline pH by addition of, for example, sodium hydroxide, potassium hydroxide or sodium carbonate followed by extraction and evaporation of solvent.

The compounds of formula (II) wherein R² is

and Y is —OR³, —SR³ or —NR⁴R⁵ are preferably derived from the corresponding compound of formula (II) wherein R² is —CN. The imino esters of formula (II) wherein R² is

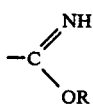

are prepared from the nitrile, R² = —CN, by reaction with a compound of formula R³OH. The reaction can be carried out under acid or alkaline conditions. When acid conditions are employed the reaction is preferably carried out by dissolving the cyano compound and at least an equimolar amount of the alkanol or phenol of formula R³OH in an appropriate aprotic solvent, such as, for example, diethyl ether, tetrahydrofuran, chloroform or methylene chloride, then saturating the solution with from two to four moles of dry hydrogen chloride at temperatures from about —10° to 25° C. The reaction is carried out under substantially anhydrous conditions. The reaction is maintained at a temperature within the above range for about 12 hours or longer periods of up to a week. The reaction mixture is then made alkaline with, for example, sodium hydroxide or potassium hydroxide and the desired product isolated by extraction and evaporation of solvent.

When alkaline conditions are employed to prepare the imino ether, the 2-(4-cyanopiperazin-1-yl)-4-amino-6,7-dimethoxyquinazoline is dissolved in an excess of a dry alkanol or phenol of formula R³OH, containing an equimolar amount of an alkali metal alkoxide or phenoxide; for example, R³ONa or R³OK. The reaction may be carried out over a wide range of temperature; however, temperatures of from about 50° to 125° C. are preferred. The reaction is ordinarily complete within a matter of from about 2 to 20 hours. The reaction mixture, cooled to room temperature, is then neutralized; for example, by addition of hydrochloric, sulfuric, acetic, formic or phosphoric acids and the mixture evaporated to dryness. The residue is partitioned between water and a water insoluble solvent; such as, for example, chloroform, methylene chloride or ethyl ether, the dried organic extracts are then evaporated to obtain the desired imino ether.

The compounds of formula (II) wherein R² is

can be prepared employing the above described acid conditions for the corresponding compounds wherein R² is

by replacing the alkanol or phenol used therein with the appropriate alkyl mercaptan or thiophenol of formula R³SH. They can also be prepared by reacting the compound of formula (II) wherein R² is —CN with an equimolar amount of R³SH in the presence of a reaction inert solvent. A similar procedure for prepating S-methyl isothiourea from cyanamid and methyl mercaptan has been described by Arndt, *Chem. Ber.*, 54, 2237 (1921). This reaction is preferably carried out at temperatures from about —10° to 50° C. and proceeds to completion in from about 1 to 10 hours. The product is isolated merely by evaporation of solvent. Examples of suitable reaction inert solvents are those provided above for Method B. An alternate method for obtaining the compounds of formula (II) wherein R² is

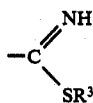

is to react the piperazine derivative of formula (V) with ammonium thiocyanate to obtain the corresponding thiocarbamyl piperazine; this may then be reacted with the appropriate halide or sulfonate, of formula $R^3B$, wherein B is selected from the group consisting of chloro, bromo, iodo, methanesulfonyloxy, benzenesulfonyloxy and p-toluenesulfonyloxy. The desired compounds are then isolated by treatment with aqueous alkali and extraction. Techniques for the reaction of amines with ammonium thiocyanate and for alkylation of thioureas are discussed in Houben-Weyl's "Methoden der Organischen Chemie", Vol. 9, 1955, pages 887–889 and 900–903.

The N-amidinopiperazines of formula (II) wherein $R^2$ is

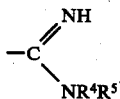

are obtained by reaction of the appropriate secondary amine $HNR^4R^5$ with an imino ester of formula (II) wherein $R^2$ is

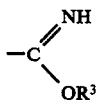

which in turn, is derived from the cyanopiperazine derivative of formula (II) wherein $R^2$ is —CN. Said imino ester and said secondary amine are combined in equimolar amounts in the presence of a reaction inert organic solvent and heated, preferably at a temperature from about 50° to 150° C. The reaction is ordinarily complete within a matter of a few hours to 48 hours or more. The desired amidino compound is recovered by standard methods, often merely by cooling the reaction mixture, filtering and washing. Examples of suitable reaction inert solvents are those provided above for Method A.

The following examples are provided to further illustrate the invention. They are not to be construed as limiting the invention in any way. Many variations are possible within the spirit of the invention.

EXAMPLE 1

2-(4-Cyanopiperazin-1-yl)-4-amino-6,7-dimethoxyquinazoline

A mixture of 10.0 g. (0.033 mole) of 2-(1-piperazinyl)-4-amino-6,7-dimethoxyquinazoline, prepared as described in U.S. Pat. No. 3,511,836, 3.54 g. (0.033 mole) of cyanogen bromide and 33 ml. of N,N-dimethylformamide was stirred under nitrogen at room temperature (20°–25° C.) for 6 hours. The precipitated solid was recovered by filtration, washed with ether and air dried to afford 11.6 g. (85%) of the hydrobromide salt of the title compound. The salt was partitioned between 250 ml. of aqueous saturated sodium bicarbonate solution and 500 ml. of chloroform. The layers were separated and the chloroform layer concentrated in vacuo to afford the free base as a dry foam, 8.3 g. (80%); M.P. 215° C. The mass spectrum reveals a molecular ion peak at M/e 314. Infrared spectrum ($CHCl_3$): peak at 4.5 μ (CN).

EXAMPLE 1A

To a solution of 8.6 g. (0.10 mole) of piperazine in 50 ml. of dry tetrahydrofuran is added at room temperature over 15 minutes a solution of 10.6 g. (0.10 mole) of cyanogen bromide in 50 ml. of the same solvent. When the addition is complete, the reaction mixture is stirred at 25° C. for 2 hours, adjusted to pH 10 with 2N aqueous sodium hydroxide solution and the organic layer is separated. The aqueous phase is extracted twice more with 100 ml. portions of tetrahydrofuran, the combined extracts are dried over anhydrous potassium carbonate then evaporated to dryness to afford 1-cyanopiperazine.

In a flask fitted with stirrer, thermometer, and drying tube is placed 100 ml. of chloroform, 12.0 g. (0.05 mole) of 4-amino-2-bromo-6,7-dimethoxyquinazoline (prepared by the method of U.S. Pat. No. 3,511,836) and 5.8 g. (0.052 mole) of 1-cyanopiperazine. The mixture is maintained at 50° C. for 24 hours after which 2N potassium hydroxide solution is added at room temperature to adjust to pH 9.5. The organic layer is separated and the aqueous phase extracted again with chloroform and the combined extracts are evaporated to dryness to obtain 2-(4-cyanopiperazin-1-yl)-4-amino-6,7-dimethoxyquinazoline.

EXAMPLE 2

2-[4-(2-Furoyl)piperazin-1-yl]-4-amino-6,7-dimethoxyquinazoline

In a 100 ml. flask equipped with thermometer and drying tube was charged 10 ml. of dry tetrahydrofuran and 0.5 ml. (6.2 mmoles) of furan. The solution was cooled to −20° C. and 2.8 ml. (6.2 mmoles) of n-butyl lithium in hexane was added. To the resulting light amber mixture was added 400 mg. (1.24 mmoles) of 2-(4-cyanopiperazin-1-yl)-4-amino-6,7-dimethoxyquinazoline dissolved in 30 ml. of dry tetrahydrofuran. After the addition was complete, the reaction mixture was allowed to warm to room temperature while stirring overnight. The reaction was quenched into 88 ml. of 2N hydrochloric acid, washed with 100 ml. of chloroform, adjusted to pH 10 with aqueous sodium hydroxide solution and extracted twice with 100 ml. portions of chloroform. The aqueous phase was concentrated in vacuo to about 2 ml. and filtered to afford 15 mg of the title compound, M.P. 263°–264° C. The infrared spectrum and thin-layer chromatography behavior were identical to that of an authentic specimen.

When the above procedure was repeated, but employing equimolar amounts of all reactants (i.e., 6.2 mmoles of 2-[4-cyanopiperazin-1-yl]-4-amino-6,7-dimethoxyquinazoline) the title compound was obtained in 37% yield.

EXAMPLE 3

2-(4-Carbethoxypiperazin-1-yl)-4-amino-6,7-dimethoxyquinazoline

In a reaction vessel equipped with stirrer, thermometer and drying tube was charged 60 ml. of isoamyl alcohol, 10 g. (0.042 mole) of 4-amino-2-chloro-6,7-dimethoxyquinazoline (prepared as described in U.S. Pat. No. 3,511,836) and 7.3 g. (0.047 mole) ethyl-N- piperazinocarboxylate (Aldrich Chemical Co.). The mixture was heated at 100° C. for 3 hours and allowed to stand overnight at room temperature. The mixture was diluted with 120 ml. of isoamyl alcohol and filtered to obtain 14.3 g. (94%) of the hydrochloride salt of the title compound, which melted sharply at 295° C.

Twelve grams of the hydrochloride salt was stirred in 100 ml. of chloroform containing two equivalents of triethylamine. After 2 hours the unreacted starting material was removed by filtration. The filtrate was washed with two 50 ml. portions of water, then concentrated to dryness to obtain 5.1 g. (48%) of the title compound.

When the above procedure is repeated but the reaction mixture maintained at 50° C. for 24 hours or at 150° C. for one hour in N,N-dimethylformamide as solvent, the results are substantially unchanged.

EXAMPLE 3A

A solution of 2.89 g. (0.01 mole) of 2-(1-piperazinyl)-4-amino-6,7-dimethoxyquinazoline in 25 ml. of 1,2-dimethoxyethane is cooled to 10° C. and a solution of 1.09 g. (0.01 mole) of ethyl chloroformate in 5 ml. of the same solvent is added dropwise over 15 minutes with stirring. The resulting mixture is allowed to warm to room temperature and stirring continued for 3 hours. The reaction mixture is poured into 25 ml. of water, adjusted to pH 9.5 with 0.5M sodium hydroxide solution and extracted with 3 × 25 ml. of methylene chloride. The extracts are concentrated to about 20 ml., filtered and to the filtrate is added 40 ml. of hexane. The precipitated product, 2-(4-carbethoxypiperazin-1-yl)-4-amino-6,7-dimethoxyquinazoline, is collected by filtration and air dried.

When the above procedure is carried out at −20° C. for 10 hours in methylene chloride as solvent or at 50° C. for 1 hour in tetrahydrofuran as solvent, the results are essentially the same.

EXAMPLE 4

When the procedure of Example 3A is repeated with the appropriate chloroformate ester, chlorothiolformate ester or N,N-disubstituted carbamyl chloride in place of ethyl chloroformate, the following compounds of formula (II) are similarly obtained.

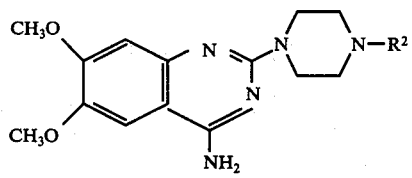

| $R_2$ |
|---|
| —COOCH$_3$ |
| —COOCH(CH$_3$)$_2$ |
| —COOCH$_2$(CH$_2$)$_2$CH$_3$ |
| —CON(CH$_3$)$_2$ |
| —CON(C$_6$H$_5$)$_2$ |
| —CONCH$_2$(CH$_2$)$_2$CH$_3$<br>    |<br>    CH$_3$ |
| —CON—C$_6$H$_5$<br>    |<br>    CH$_3$ |
| —CON—CH$_2$(CH$_2$)$_2$CH$_3$<br>    |<br>    C$_6$H$_5$ |
| —COSCH$_3$ |

| $R_2$ |
|---|
| —COSCH(CH$_3$)$_2$ |
| —COSCH$_2$CH(CH$_3$)$_2$ |
| —COSCH$_2$(CH$_2$)$_2$CH$_3$ |
| —COSC$_6$H$_5$ |
| —COOC$_6$H$_5$ |

When the procedure of Example 3 is repeated with the appropriately substituted piperazine in place of ethyl N-piperazinocarboxylate, the above compounds are also obtained.

Methyl chloroformate, n-butyl chloroformate, N,N-dimethylcarbamyl chloride, N,N-diphenylcarbamyl chloride and N-methyl,N-phenylcarbamyl chloride are commercially available. The remaining chloroformates, chlorothiolformates and N,N-disubstituted carbamyl chlorides are prepared by reaction of phosgene and the appropriate alcohol, phenol, mercaptan or secondary amine by the procedures of Bergmann et al., *Chem. Ber.*, 65, 1192 (1932); Jensen, *Jour. Prakt, Chim.*, 148, 105 (1937) or Boon, *Jour. Chem. Soc.*, 313 (1947), respectively.

EXAMPLE 5

A solution of 6.8 g. (0.10 mole) of furan in 100 ml. of dry ether is cooled to −60° C. while sweeping the solution with dry nitrogen. Under anhydrous conditions, 0.01 mole of a 15% by weight solution of butyllithium in hexane is added and the resulting mixture is stirred for 10–15 minutes. To this is then added 3.60 g. (0.01 mole) of 2-[4-(N,N-dimethylcarbamyl)piperazin-1-yl]-4-amino-6,7-dimethoxyqunazoline in 25 ml. of ethyl ether. The resulting mixture is stirred at −60° C. for 2 hours, then allowed to stir overnight at room temperature. The mixture is poured into 100 ml. of 2N hydrochloric acid containing an equal volume of ice, extracted with two 50 ml. portions of chloroform and the extracts discarded. The aqueous layer is adjusted to pH 10 with sodium hydroxide solution, then extracted with 3 × 50 ml. of chloroform. The extracts are dried over sodium sulfate then concentrated to a small volume. Upon addition of hexane 2-[4-(2-furoyl)piperazin-1-yl]-4-amino-6,7-dimethoxyquinazoline is precipitated and filtered.

When the above procedure is carried out at −20° instead of −60° C., the results are substantially unchanged.

EXAMPLE 6

4-(4-Amino-6,7-dimethoxyquinazolin-2-yl)piperazine-1-imidic Acid Ethyl Ester

To a dry flask equipped with stirrer, thermometer and reflux condenser is placed 25 ml. of ethanol and sodium metal, 0.253 g. (0.011 g. atom) is added in portions. When the sodium is completely reacted, 3.14 g. (0.01 mole) of 2-(4-cyanopiperazin-1-yl)-4-amino-6,7-dimethoxyquinazoline is added and the resulting mixture is refluxed for 5 hours. After cooling to room temperature, glacial acetic acid is added to neutralize the mixture. After evaporation to dryness, 25 ml. of water and 50 ml. of chloroform are added to the residue. The mixture is transferred to a separatory funnel and the chloroform layer washed again with water, dried over anhydrous sodium sulfate then concentrated to dryness to provide the title compound.

When the reaction is carried out at 50° C. for 20 hours, the results are substantially unchanged.

EXAMPLE 6A

When the above procedure is repeated, but employing n-butanol in place of the ethanol used therein and the reaction mixture is maintained at 125° C. for 2 hours then worked up in the same manner, 4-(4-amino-6,7-dimethoxyquinazolin-2-yl)piperazine-1-imidic acid n-butyl ester is obtained.

EXAMPLE 7

4-(4-Amino-6,7-dimethoxyquinazolin-2-yl)piperazine-1-imidic Acid Methyl Ester

Under anhydrous conditions, 6.3 g. (0.02 mole) of 2-(4-cyanopiperazin-1-yl)-4-amino-6,7-dimethoxyquinazoline is dissolved in 150 ml. of ethyl ether and 1.8 ml. (0.044 mole) of reagent grade methanol is added. The solution is cooled to 0° C. and anhydrous hydrogen chloride is added until the solution is acid to Congo red paper. The resulting mixture is stored at 0° C. for 2 hours, then allowed to warm to room temperature (25° C) overnight. The reaction mixture is made alkaline with 2N sodium hydroxide, the ether layer separated, washed with 2 × 50 ml. of water, dried over anhydrous magnesium sulfate and evaporated to dryness to obtain the title compound.

When the procedure is carried out at −10° C. for 48 hours, the title compound is similarly obtained.

EXAMPLE 8

4-(4-Amino-6,7-dimethoxyquinazolin-2-yl)piperazine-1-thio-imidic Acid, S-n-butyl Ester To a solution of 6.3 g. (0.02 mole) of 2-(4-cyanopiperazin-1-yl)-4-amino-6,7-dimethoxyquinazoline in 75 ml. of diethyleneglycol dimethyl ether is added dropwise over 15 minutes a solution of 1.8 g. (0.02 mole) n-butyl mercaptan in 25 ml. of the same solvent. The resulting mixture is stirred at 20°-25° C. for 2 hours, then the solvent is removed in vacuo. The residue is triturated with ethyl ether, filtered and dried to obtain the title compound.

EXAMPLE 9

By employing the appropriate alcohol, phenol or mercaptan as starting material and following the procedure of Example 6 or Example 7 for those cases where Y is O-alkyl or —OC$_6$H$_5$ and the procedure of Example 7 or Example 8 for those where Y is S-alkyl or —SC$_6$H$_5$, the following compounds are obtained.

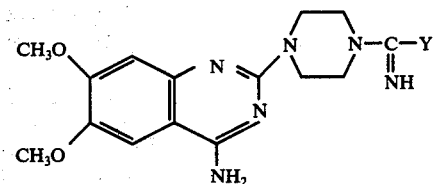

| Y |
|---|
| —OCH(CH$_3$)$_2$ |
| —OC$_6$H$_5$ |
| —OCH$_2$CH(CH$_3$)$_2$ |
| —SCH$_3$ |
| —SCH$_2$CH$_2$CH$_3$ |
| —SCH$_2$CH(CH$_3$)$_2$ |
| —SC$_6$H$_5$ |

EXAMPLE 10

4-(4-Amino-6,7-dimethoxyquinazolin-2-yl)-1-(N-methyl-N-phenyl-amidino)piperazine To a flask containing 3.47 g. (0.01 mole) of 4-(4-amino-6,7-dimethoxyquinazolin-2-yl)piperazine-1-imidic acid methyl ester is added 1.07 g. (0.01 mole) of N-methylaniline dissolved in 10 ml. of ethanol. The resulting mixture is refluxed for 18 hours and cooled to room temperature. The precipitated product is recovered by filtration, washed with ether and dried to afford the title compound.

When an equivalent amount of 4-(4-amino-6,7-dimethoxyquinazolin-2-yl)piperazine-1-imidic acid n-butyl ester is used in place of the corresponding methyl ester in the above procedure the results are substantially the same.

When the above procedure is repeated but the reaction mixture maintained at 50° C. for 48 hours or at 150° C. employing N,N-dimethylformamide as solvent, the results are substantially the same.

EXAMPLE 11

When the procedure of Example 10 is repeated but using an equimolar amount of the appropriate amine, R$^4$R$^5$NH, in place of N-methyl aniline, the following compounds are similarly obtained.

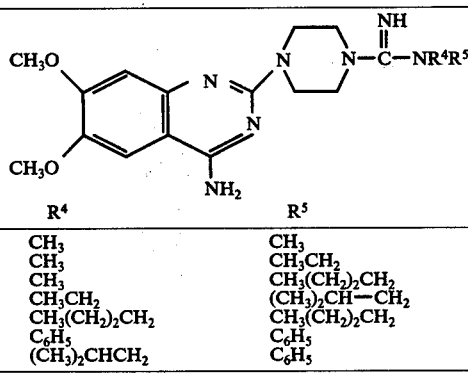

| R$^4$ | R$^5$ |
|---|---|
| CH$_3$ | CH$_3$ |
| CH$_3$ | CH$_3$CH$_2$ |
| CH$_3$ | CH$_3$(CH$_2$)$_2$CH$_2$ |
| CH$_3$CH$_2$ | (CH$_3$)$_2$CH—CH$_2$ |
| CH$_3$(CH$_2$)$_2$CH$_2$ | CH$_3$(CH$_2$)$_2$CH$_2$ |
| C$_6$H$_5$ | C$_6$H$_5$ |
| (CH$_3$)$_2$CHCH$_2$ | C$_6$H$_5$ |

EXAMPLE 12

2-Furylsodium is prepared by the method of Morton et al., *J. Am. Chem. Soc.*, 68, 93 (1946) as follows:

2.3 g. (0.10 g. atom) of sodium sand and 10.7 g. of n-amyl chloride in 200 ml. of ethyl ether are stirred vigorously at −5° to 0° C. until the sodium is consumed. Then 10 g. of reagent grade toluene is added and the mixture is allowed to warm to reflux and maintained at the reflux temperature for 3 hours. The resulting benzyl sodium is treated with 13.6 g. (0.2 mole) of furan and stirred at room temperature for 1 hour to provide the 2-furyl-sodium.

To the above mixture is added slowly at −20° C., 32.9 g. (0.10 mole) of 2-(4-carbethoxypiperazin-1-yl)-4-amino-6,7-dimethoxyquinazoline dissolved in 300 ml. of ethyl ether. The reaction mixture is stirred at −20° C. for 2 hours, then allowed to warm to room temperature. The resulting mixture is hydrolyzed by addition of 100 ml. of water, and the ether layer separated. The aqueous layer is extracted with 300 ml. of ether and the combined extracts are dried over anhydrous magnesium sulfate. Evaporation of solvent affords 2-[4-(2-furoyl)-piperazin-1-yl]-4-amino-6,7-dimethoxyquinazoline which can be further pruified if desired by silica gel column chromatography.

EXAMPLE 13

2-(4-Benzoylpiperazin-1-yl)-4-amino-6,7-dimethoxyquinazoline

Under anhydrous conditions, a solution of 5.43 g. (0.03 mole) of phenylmagnesium bromide in 100 ml. of tetrahydrofuran is swept with dry nitrogen and a solution of 3.15 g. (0.01 mole) of 2-(4-cyanopiperazin-1-yl)-4-amino 6,7-dimethoxyquinazoline in 75 ml. of the same solvent is added dropwise over 30 minutes at room temperature. When the addition is complete, the reaction mixture is heated at 65° C. for 6 hours, then allowed to stand at room temperature overnight. To the reaction mixture is then added 25 ml. of 2N hydrochloric acid and stirring is continued for an additional 30 minutes. The reaction mixture is then made alkaline with sodium hydroxide solution and the organic layer separated. The aqueous layer is extracted with 2 × 100 ml. of tetrahydrofuran and the combined organic layers are dried over anhydrous magnesium sulfate and evaporated to dryness to obtain the crude title compound which can be further purified by crystallization from ethanol or by column chromatography on silica gel.

EXAMPLE 14

2-[4-(2-Thenoyl)piperazin-1-yl]-4-amino-6,7-dimethoxyquinazoline

In a flask fitted with mechanical stirrer, reflux condenser, dropping funnel and nitrogen inlet, are placed 0.73 g. (0.03 g. atom) of magnesium turnings and 75 ml. of ethyl ether. With stirring, is added dropwise 6.3 g. (0.03 mole) of 2-iodothiophene prepared by the method of Organic Syntheses, Coll. vol. 4, John Wiley and Sons, Inc., New York, 1963, page 545) in 25 ml. of ethyl ether. During the addition the reaction mixture warms to reflux. When the addition is complete, refluxing is continued until most of the magnesium has been consumed. Then a solution of 3.60 g. (0.01 mole) of 2-[4-N,N-dimethylcarbamyl)piperazin-1-yl]-4-amino-6,7-dimethoxyquinazoline in 50 ml. of ether is added dropwise over 30 minutes and the mixture heated at reflux for 8 hours. The reaction mixture is then worked up as described in Example 13 to obtain the title compound.

EXAMPLE 15

When 2-chlorofuran, 2-bromofuran, or 2-iodofuran is employed in place of the 2-iodothiophene in the procedure of Example 14, 2-[4-(2-furoyl)piperazin-1-yl]-4-amino-6,7-dimethoxyquinazoline is similarly obtained.

The 2-chlorofuran and 2-bromofuran are obtained from the corresponding 5-halofuran-2-carboxylic acid by the method of Shepard et al., J. Am. Chem. Soc., 52, 2083, (1930). 2-Iodofuran is provided by the procedure of Gilman et al., J. Am. Chem. Soc., 54, 733 (1932).

EXAMPLE 16

By employing the appropriate starting materials in each case and employing the procedures of Examples 2, 5, 12 and 13, the following compounds of formula (I) are similarly obtained.

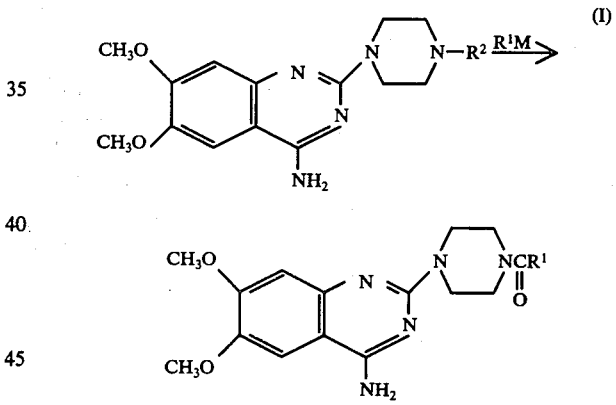

| By Procedure of Example | R¹M | R² | Solvent# | Reaction Temperature, ° C. |
|---|---|---|---|---|
| 2 | 3-furyllithium* | —COSCH₃ | ethyl ether | −80° |
| 2 | C₆H₅Li | —COSCH₂CH(CH₃)₂ | THF | −60° |
| 2 | 2-thienyllithium* | —COOCH₂(CH₂)₂CH₃ | monoglyme | −20° |
| 2 | 3-thienyllithium* | —COOCH₃ | THF | −30° |
| 2 | 2-furyllithium | —CONCH₂(CH₂)₂CH₃<br>      \|<br>     CH₃ | THF | −20° |
| 2 | 2-furyllithium | —CON(CH₂(CH₂)₂CH₃)₂ | isopropyl ether | −25° |
| 5 | C₆H₅Li* | —CON(C₆H₅)₂ | ethyl ether | −30° |
| 5 | C₆H₅Li | —CON—C₆H₅<br>    \|<br>   CH₃ | diglyme | −20° |
| 5 | 2-furyllithium | —COCH₃<br>   \|\|<br>   NH | THP | −20° |
| 5 | 2-thienyllithium | —COCH₂CH(CH₃)₂<br>   \|\|<br>   NH | anisole | −20° |

-continued

| By Procedure of Example | R¹M | R² | Solvent# | Reaction Temperature, °C. |
|---|---|---|---|---|
| 5 | $C_6H_5Li$ | —CSC$_6$H$_5$<br>‖<br>NH | ethyl ether | −20° |
| 5 | 2-furyllithium | —CSCH$_2$CH(CH$_3$)$_2$<br>‖<br>NH | ethyl ether | −80° |
| 5 | $C_6H_5Li$ | —CN(CH$_3$)$_2$<br>‖<br>NH | ethyl ether | −20° |
| 5 | 2-thienyllithium | —CN(CH$_3$)—C$_6$H$_5$<br>‖<br>NH | ethyl ether | −60° |
| 12 | 2-thienylsodium* | —CN(CH$_2$(CH$_2$)$_2$CH$_3$)$_2$<br>‖<br>NH | ethyl ether | −20° |
| 12 | 2-furylsodium | —CN(CH$_3$)CH$_2$(CH$_2$)$_2$CH$_3$<br>‖<br>NH | THF | 25° |
| 12 | 2-furylsodium | —CSCH$_3$<br>‖<br>NH | ethyl ether | 0° |
| 12 | 2-furylsodium | —CCH$_2$(CH$_2$)$_2$CH$_3$<br>‖<br>NH | ethyl ether | 10° |
| 12 | $C_6H_5Na$* | —COCH$_2$CH(CH$_3$)$_2$<br>‖<br>NH | benzene | 25° |
| 12 | $C_6H_5Na$ | —COC$_6$H$_5$<br>‖<br>NH | THF | 65° |
| 12 | 2-furylsodium | —CONCH$_2$(CH$_2$)$_2$CH$_3$<br>\|<br>C$_6$H$_5$ | ethyl ether | 35° |
| 12 | 2-furylsodium | —CONCH$_2$(CH$_2$)$_2$CH$_3$<br>\|<br>CH$_3$ | ethyl ether | 35° |
| 12 | 2-furylsodium | —CONC$_6$H$_5$<br>\|<br>CH$_3$ | ethyl ether | 25° |
| 12 | 2-furylsodium | —CON(C$_6$H$_5$)$_2$ | ethyl ether | 35° |
| 12 | 2-furylsodium | —COSC$_6$H$_5$ | THF | −60° |
| 12 | 2-furylsodium | —COSCH$_2$CH(CH$_3$)$_2$ | ethyl ether | −20° |
| 12 | 2-furylsodium | —COOCH$_3$ | ethyl ether | 10° |
| 12 | 2-furylsodium | —COOCH$_2$(CH$_2$)$_2$CH$_3$ | ethyl ether | 25° |
| 12 | 2-furylsodium | —CN | ethyl ether | −10° |
| 13 | 2-furyl-MgCl | —COOC$_6$H$_5$ | ethyl ether | 35° |
| 14 | $C_6H_5MgBr$ | —COOCH$_2$(CH$_2$)$_2$CH$_3$ | THF | 65° |
| 14 | $C_6H_5MgBr$ | —COSCH$_3$ | ethyl ether | 35° |
| 14 | 2-furyl-MgBr | —COSCH(CH$_3$)$_2$ | ethyl ether | 25° |
| 14 | 2-furyl-MgI | —CON(CH$_2$(CH$_2$)$_2$CH$_3$)$_2$ | THF | 65° |
| 14 | 2-thienyl-MgI | —CON(C$_6$H$_5$)$_2$ | ethyl ether | 35° |
| 14 | 3-thienyl-MgBr | —CON(CH$_3$)—C$_6$H$_5$ | ethyl ether | 25° |
| 14 | $C_6H_5MgI$ | —COCH$_3$<br>‖<br>NH | ethyl ether | 35° |
| 14 | 2-furyl-MgBr | —COCH$_2$CH(CH$_3$)$_2$<br>‖<br>NH | ethyl ether | 25° |
| 14 | 2-furyl-MgBr | —COCH$_3$<br>‖<br>NH | THF | 40° |
| 14 | 2-furyl-MgBr | —CSCH$_3$<br>‖<br>NH | THF | 65° |
| 14 | 2-furyl-MgBr | —CSCH$_2$(CH$_2$)$_2$CH$_3$<br>‖<br>NH | ethyl ether | 35° |
| 14 | 2-furyl-MgBr | —CN(CH$_3$)$_2$<br>‖<br>NH | THF | 65° |
| 14 | 2-furyl-MgBr | —CN(C$_6$H$_5$)$_2$<br>‖<br>NH | THF | 65° |
| 14 | $C_6H_5MgBr$ | —CN(C$_6$H$_5$)CH$_2$CH(CH$_3$)$_2$<br>‖<br>NH | ethyl ether | 35° |
| 14 | $C_6H_5MgBr$ | —CN(CH$_3$)—C$_6$H$_5$<br>‖<br>NH | ethyl ether | 35° |
| 14 | 2-furyl-MgBr | —C—NCH$_2$(CH$_2$)$_2$CH$_3$<br>‖ \|<br>NH CH$_3$ | ethyl ether | 35° |

| By Procedure of Example | R¹M | R² | Solvent# | Reaction Temperature, °C. |
|---|---|---|---|---|
| 12 | C₆H₅Na* | —CN(C₆H₅)₂ ‖ NH | benzene | 25° |

THF is tetrahydrofuran; monoglyme is ethyleneglycol dimethylether; diglyme is diethyleneglycol dimethylether; THP is tetrahydropyran.

*3-Furyllithium is prepared from n-butyllithium and 3-bromofuran in ether at −60° C. 2-Thienyllithium and 3-thienyllithium are prepared in the same manner from 2-bromothiophene and 3-bromothiophene, respectively. The bromofuran and bromothiophenes are available commercially from Aldrich Chemical Co.

The preparation of phenyllithium and phenylsodium are discussed in Fieser, "Reagents for Organic Synthesis," John Wiley and Sons, Inc., 1967, pages 845, 848 and references therein. 2-Thienylsodium is prepared from 2-bromothiophene and powdered sodium in benzene-ether.

What is claimed is:

1. A process for preparing a product of the formula

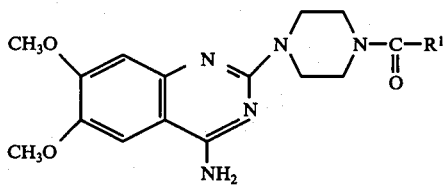

which comprises the steps of
a. contacting one mole of a first reactant of the formula

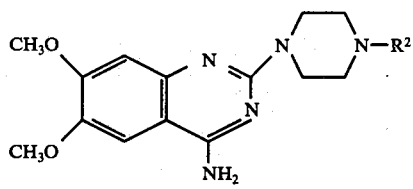

wherein
R² is a member selected from the group consisting of —CN,

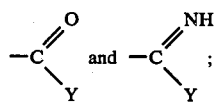

Y is a member selected from the group consisting of —OR³, —SR³ and —NR⁴R⁵;

R³ is a member selected from the group consisting of alkyl having from one to four carbon atoms and phenyl;

R⁴ and R⁵ are the same or different and are each selected from the group consisting of alkyl having from one to four carbon atoms and phenyl;

with from about one to three moles of a second reactant of the formula

R¹M wherein R¹ is a member selected from the group consisting of furyl, phenyl and thienyl;

and M is a member selected from the group consisting of Li, Na and MgX where X is Cl, Br or I;

under substantially anhydrous conditions in the presence of a reaction inert organic solvent at a temperature from about −80° to 65° C.; and b. hydrolyzing the reaction mixture obtained in step a.

2. The process according to claim 1 wherein R² is —CN or —CONR⁴R⁵ and M is Li.

3. The process according to claim 2 wherein said reactants are contacted at a temperature from about −60° to −20 C.

4. The process according to claim 2 wherein equimolar amounts of said reactants are contacted.

5. The process according to claim 2 wherein R⁴ and R⁵ are each methyl.

6. The process according to claim 2 wherein R⁴ and R⁵ are each phenyl.

7. The process according to claim 1 wherein R¹ is 2-furyl.

* * * * *